(12) United States Patent
Kitagawa

(10) Patent No.: US 10,140,275 B2
(45) Date of Patent: Nov. 27, 2018

(54) MESSAGE INFORMATION GENERATING APPARATUS, OUTGOING CALL CONTROL APPARATUS, MESSAGE INFORMATION GENERATING METHOD, AND OUTGOING CALL CONTROL METHOD

(71) Applicant: FUJITSU LIMITED, Kawasaki-shi, Kanagawa (JP)

(72) Inventor: Katsuhiro Kitagawa, Sakai (JP)

(73) Assignee: FUJITSU LIMITED, Kawasaki (JP)

( * ) Notice: Subject to any disclaimer, the term of this patent is extended or adjusted under 35 U.S.C. 154(b) by 162 days.

(21) Appl. No.: 15/434,619

(22) Filed: Feb. 16, 2017

(65) Prior Publication Data

US 2017/0242834 A1 Aug. 24, 2017

(30) Foreign Application Priority Data

Feb. 24, 2016 (JP) ................................ 2016-033142

(51) Int. Cl.
*G06F 3/048* (2013.01)
*G06F 17/24* (2006.01)
*G06F 3/0488* (2013.01)
*G06F 19/00* (2018.01)

(52) U.S. Cl.
CPC ........ *G06F 17/242* (2013.01); *G06F 3/04883* (2013.01); *G06F 19/3418* (2013.01)

(58) Field of Classification Search
CPC ..... H04L 51/28; H04L 63/0407; H04L 51/24; H04L 67/306; G06F 19/00; G06F 19/3418; G06F 9/50
See application file for complete search history.

(56) References Cited

U.S. PATENT DOCUMENTS

| 8,125,689 B2 | 2/2012 | Morita et al. |
| 2010/0149206 A1 | 6/2010 | Shigehisa et al. |
| 2012/0102122 A1* | 4/2012 | Byrnes ................ G06Q 10/107 709/206 |

(Continued)

FOREIGN PATENT DOCUMENTS

| JP | 9-282309 A | 10/1997 |
| JP | 2002-366343 A | 12/2002 |
| JP | 2006-65721 A | 3/2006 |

(Continued)

*Primary Examiner* — Linh K Pham
(74) *Attorney, Agent, or Firm* — Westerman, Hattori, Daniels & Adrian, LLP

(57) ABSTRACT

Disclosed is a non-transitory computer-readable recording medium having stored therein a message information generating program, which when processed by one or more processors, causes a computer to execute a process. The process includes acquiring first information having both a character string input by handwriting and a character color related to the character string input by the handwriting, specifying a form of the character string based on the acquired first information, specifying an address associated with the specified form by referring to a storage configured to store an address of a message destination in association with a form of a character string, and generating message information with the specified address as a destination, the message information including second information corresponding to the character string.

16 Claims, 9 Drawing Sheets

(56) References Cited

U.S. PATENT DOCUMENTS

| | | | |
|---|---|---|---|
| 2014/0201624 A1* | 7/2014 | Clark | G06F 17/248 715/243 |
| 2016/0103504 A1* | 4/2016 | Kang | G06F 3/04883 345/173 |

FOREIGN PATENT DOCUMENTS

| | | |
|---|---|---|
| JP | 2009-5194 A | 1/2009 |
| JP | 2010-146086 A | 7/2010 |

* cited by examiner

FIG.4A

| DATE AND TIME | HANDWRITTEN CONTENT | TRANSMISSION-CALLING HISTORY | REFERENCE HISTORY | ... |
|---|---|---|---|---|

| FORM/ SPECIAL INPUT | TYPE | DESTINATION NAME | ADDRESS/ PHONE NUMBER | FIXED MESSAGE | AUTHEN- TICATION INFORMATION | ... |
|---|---|---|---|---|---|---|

| DATE AND TIME | TRANSMISSION/ RECEPTION TYPE | COUNTERPART ADDRESS/ PHONE NUMBER | MESSAGE CONTENT | UNREAD/READ | ... |
|---|---|---|---|---|---|

| APPARATUS NUMBER | CONNECTION HISTORY | ... |
|---|---|---|

216

Mr. XX ate simmered meat and potatoes for supper yesterday.

Mr. XX has had a fever since yesterday!

If Mr. XX still appears sick at night, please contact Dr. YY.

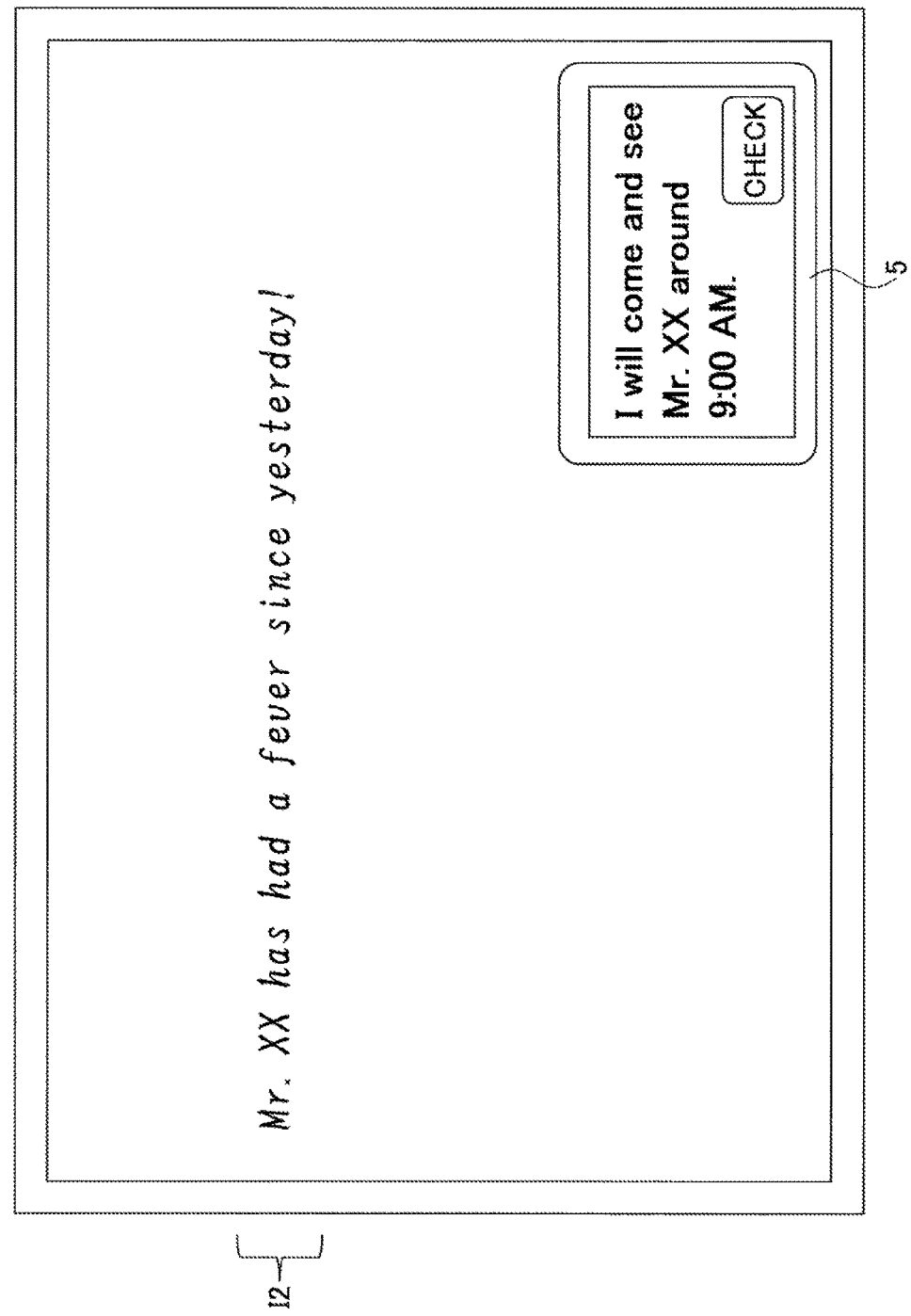

MESSAGE INFORMATION GENERATING APPARATUS, OUTGOING CALL CONTROL APPARATUS, MESSAGE INFORMATION GENERATING METHOD, AND OUTGOING CALL CONTROL METHOD

CROSS-REFERENCE TO RELATED APPLICATION

This patent application is based upon, and claims the benefit of priority of Japanese Patent Application No. 2016-033142 filed on Feb. 24, 2016, the entire contents of which are incorporated herein by reference.

FIELD

The disclosures discussed herein relate to a message information generating apparatus, an outgoing call control apparatus, a message information generating method, and an outgoing call control method.

BACKGROUND

Primary doctors (home-visiting doctors), home-visiting nurses and care managers typically use a "communication notebook" to leave handwritten notes for communicating with families of the care receivers as part of a security and protection care of the elderly and the home-bound patients. For example, a communication notebook may be used when the care manager leaves a message for other related people about the appetite and physical condition of the elderly people and home-bound patients, when the family leaves a message for the care manager about the storage of the foods, and when the care manager leaves a message for the family about what the care manager wishes the family to prepare.

A paper-based communication notebook may be convenient because anyone can handle the communication notebook in terms of its operability; however, the communication notebook may be inconvenient because one needs to go to the place where the communication notebook is. Thus, the communication notebook may lack a real time property (or low responsiveness). Thus, there is increasing demand for digitizing the communication notebook and the like, leading to a technology involving communications utilizing remarkably spreading recent smartphones.

Meanwhile, there is disclosure on an information transmission system for having communication between the school and the parental guardian (e.g., see Patent Document 1).

RELATED ART DOCUMENT

Patent Document

Patent Document 1: Japanese Laid-open Patent Publication No. 2006-65721

SUMMARY

According to an aspect of the embodiments, there is provided a non-transitory computer-readable recording medium having stored therein a message information generating program, which when processed by one or more processors, causes a computer to execute a process. The process includes acquiring first information having both a character string input by handwriting and a character color related to the character string input by the handwriting; specifying a form of the character string based on the acquired first information; specifying an address associated with the specified form by referring to a storage configured to store an address of a message destination in association with a form of a character string; and generating message information with the specified address as a destination, the message information including second information corresponding to the character string.

The object and advantages of the invention will be realized and attained by means of the elements and combinations particularly pointed out in the appended claims.

It is to be understood that both the foregoing general description and the following detailed description are exemplary and explanatory and are not restrictive of the invention.

Additional objects and advantages of the embodiments will be set forth in part in the description which follows, and in part will be obvious from the description, or may be learned by practice of the invention.

BRIEF DESCRIPTION OF THE DRAWINGS

FIGS. 4A to 4D are diagrams illustrating examples of data structures of various databases;

FIG. 9 is a diagram illustrating a display example of a message from outside.

DESCRIPTION OF EMBODIMENTS

Many elderly people are not used to operations of smartphones and the like, or everyone is not necessarily accustomed to the operations even if they are not elderly. Moreover, when one desires to transmit some message by a smartphone or the like, he or she needs to select an appropriate destination according to the details of the message, which may further complicate the smartphone operations. When sending urgent messages, in particular, he or she needs to operate a smartphone in a hurry, which may make the operations even more difficult, leading to an erroneous operation.

The following illustrates preferred embodiments with reference the accompanying drawings.

Configuration

Figure 1:
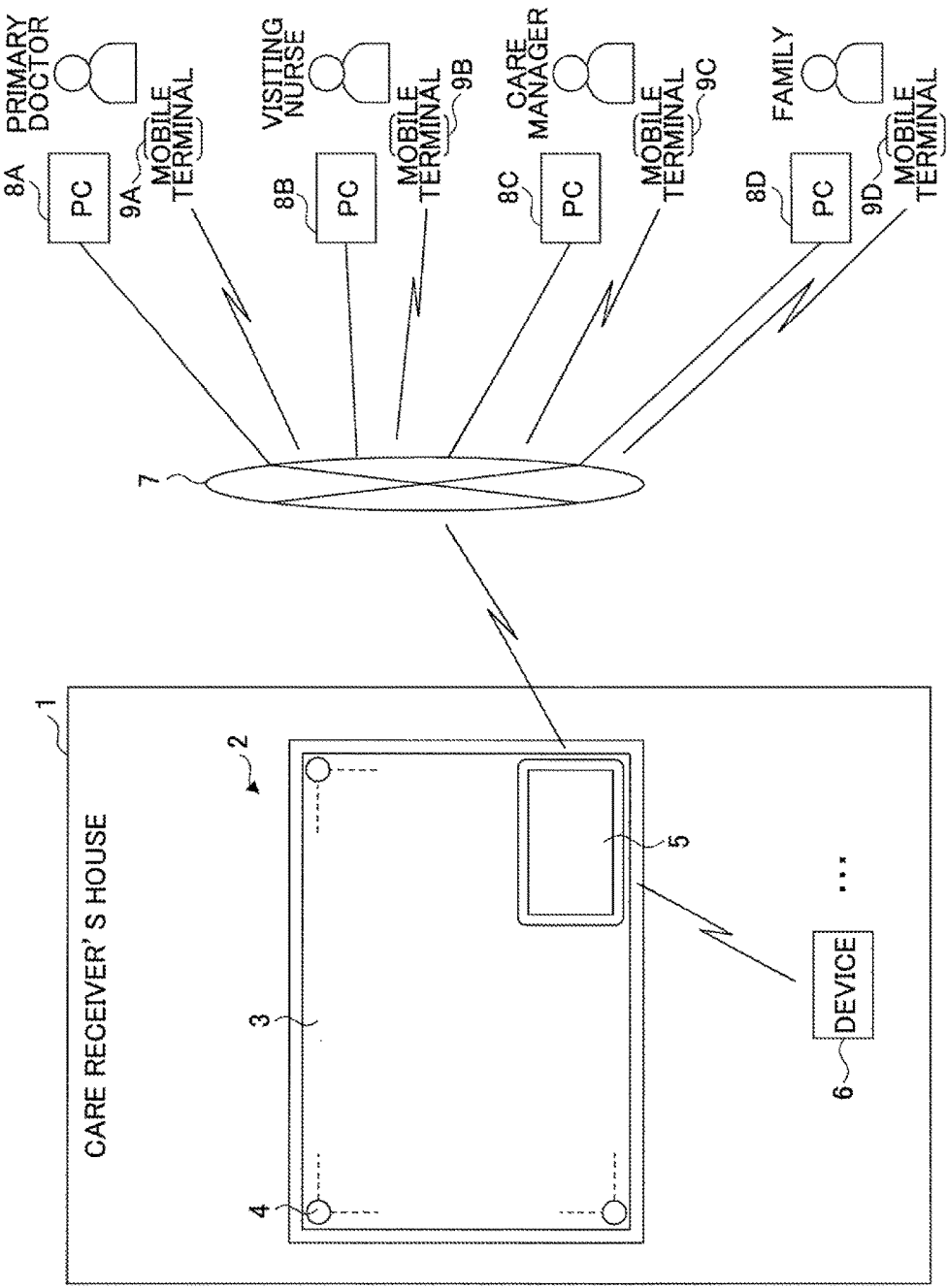
FIG. 1 is a diagram illustrating an example of a system configuration according to an embodiment.

FIG. 1 is a diagram illustrating an example of a system configuration according to an embodiment. In FIG. 1, a message board 2 is provided on a wall or the like inside the entrance at a care receiver's house 1, which is a residence of an elderly person, a home-bound patient and the like. The message board 2 includes a whiteboard 3 having sensors 4 configured to detect handwritten content written with a ink pen on the whiteboard 3 and a tablet 5 at a corner. The sensors 4 are coupled to the tablet 5 wirelessly or with wire.

The sensors 4 may be used for directly imaging a handwritten surface of the whiteboard 3 in color, or acquiring a color of the pen and coordinates of a contact part of the pen. The tablet 5 includes a coupling function to couple to a network 7 and a display function to display a message received from outside on the message board 2, and is configured to perform information processing in the message board 2. The tablet 5 may use a built-in telephone device (telephone function) to transmit an outgoing call or may control a telephone device in the care receiver's house 1 to transmit an outgoing call. In addition, the tablet 5 provides a wireless environment (e.g., a Wi-Fi environment) in the care receiver's house 1, and has a function to wirelessly couple to a device 6 such as a weight scale, a blood pressure monitor, a thermometer, or the like. The message board 2 is designed to perform communications with smart devices, and infrastructure such as the Internet or cable television is thus not required for each care receiver's house 1. This makes it possible to reduce the burden on individuals and to reduce the cost of infrastructure development by local governments and the like.

The personal computers (PCs) 8 (8A, 8B, 8C and 8D) and mobile terminals 9 (9A, 9B, 9C and 9D) such as smartphones or tablets of care giving associates including a primary doctor, a visiting-nurse, a care manager, and the family are configured to be coupled to the tablet 5 of the message board 2 in the care receiver's house 1 via the network 7. Note that it is not necessary for all the associates to be able to use the PC 8 and the mobile terminal 9. In addition, the destinations of the phone calls from the tablet 5 other than those associates described above may include the fire station, the hospital, and the police.

Figure 2:
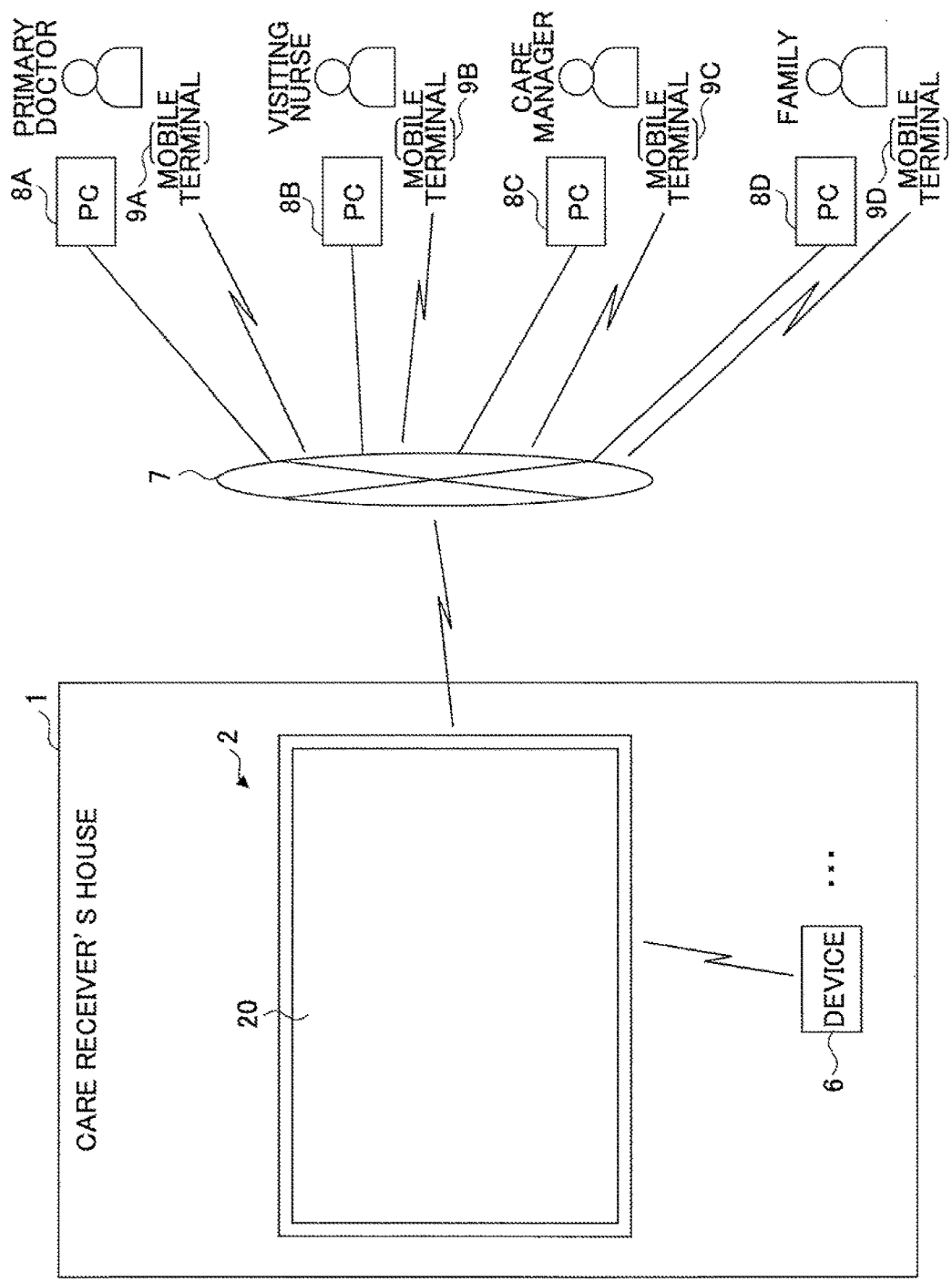
FIG. 2 is a diagram illustrating another example of a system according to an embodiment.

FIG. 2 is a diagram illustrating another example of the system configuration. In this example, the message board 2 is composed of an electronic whiteboard apparatus 20 having a wireless access function. A flat part of the electronic whiteboard apparatus 20 may be handwritten input with an electronic pen and may also serve as a display. The handwritten input may be made with an ink pen instead of the electronic pen. It is not necessary for an entire flat part of the electronic whiteboard apparatus 20 to serve as a display; the flat part of the electronic whiteboard apparatus 20 may partially serve as a display. Other parts of the system configuration are similar to those illustrated in FIG. 1.

Figure 3:
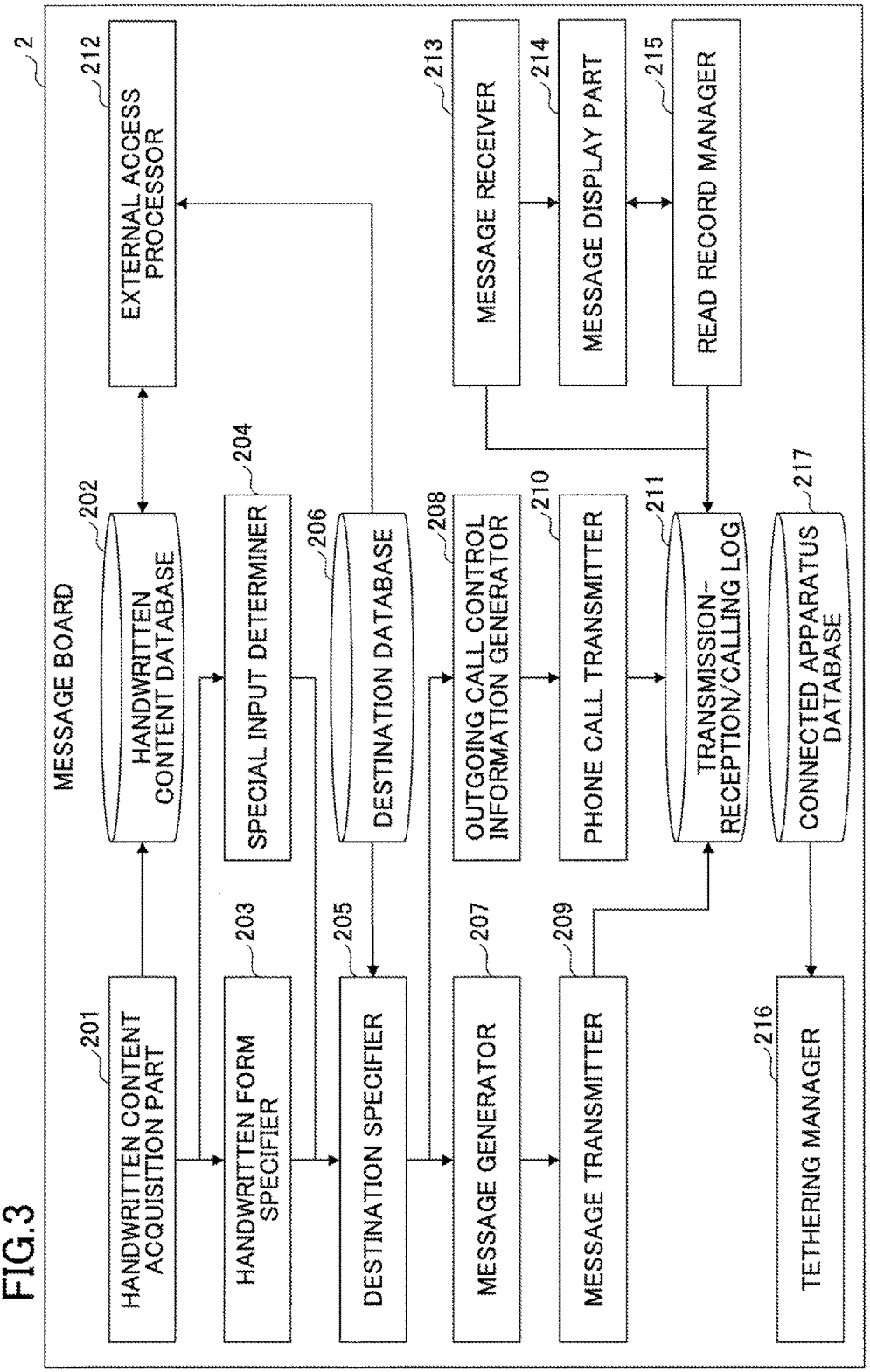
FIG. 3 is a diagram illustrating an example of a functional configuration of a message board.

FIG. 3 is a diagram illustrating an example of a functional configuration of the message board 2. In FIG. 3, the message board 2 includes a handwritten content acquisition part 201, a handwritten content database 202, a handwritten form specifier 203, a special input determiner 204, a destination specifier 205, a destination database 206, a message generator 207, an outgoing call control information generator 208, a message transmitter 209, a phone call transmitter 210, and a transmission-reception/calling log 211. The handwritten content acquisition part 201 is configured to acquire a content handwritten on the message board 2 and register the handwritten content in the handwritten content database 202. The handwritten content may be acquired as an image or trajectory information, or may be acquired as character information obtained by character recognition. FIGS. 4A to 4D illustrate examples of the data structure of the handwritten content database 202, which includes items such as "date and time", a "handwritten content", a "transmitting-calling history", and a "reference history". The "date and time" indicate the date and time information on which the handwritten content was acquired. The "handwritten content" includes image information, trajectory information or character information indicating the handwritten content. Note that the handwritten content also includes color information of the pen that was used for inputting the handwritten content for a later process. The "transmitting-calling history" includes history information indicating that a message has been transmitted to the associates or an outgoing call has been made to the associates, based on the handwritten content. The "reference history" includes history information indicating accesses to the handwritten content from the associates.

Referring back to FIG. 3, the handwritten form specifier 203 is configured to specify a "form" or a "special input" from a handwritten content newly acquired by the handwritten content acquisition part 201. The form specifies, for example, what color is used in handwriting among the predetermined color corresponding to the contact address. The special input determiner 204 is configured to specify characters, marks, symbols, and the like of the "special input" from the handwritten content newly acquired by the handwritten content acquisition part 201. Examples of the special input include "x" indicating an emergency, "Δ" indicating an alert, and the like. The destination specifier 205 is configured to refer to the destination database 206 to acquire an address of a destination in association with the form specified by the handwritten form specifier 203 or the special input specified by the special input determiner 204. FIGS. 4A to 4D indicate respective examples of data structures of the destination database 206 that includes items of a "form/special input", a "type", a "destination name", an "address/phone number", a "fixed message", and an "authentication information". The "form/special input" indicates details of a form or a special input. Examples of the form include a "red character", a "blue character" and the like, and examples of the "special input" includes "o", "x" and the like. The "type" indicates whether the message is transmitted by mail or by phone. The "destination name" indicates a name of an associate such as the primary doctor, the visiting nurse, the care manager, the family or the like, or name of the fire station, the hospital, the police or the like. The "address/phone number" indicates an address of a message (mail) destination or a phone number of a calling destination (an outgoing call destination). For example, the form indicating the "red character" indicates setting of transmission of the message for the address of the primary doctor, the form indicating the "blue character" indicates setting of transmission of the message for the address of the care manager, the special input indicating "x" indicates setting of making a phone call to the phone number of the fire station (ambulance), and the special input indicating "Δ" indicates setting of making a phone call to the phone number of the family. The "fixed message" indicates a fixed phrase to be included in a message. The "fixed message" for an outgoing phone call indicates a voice message. The "authentication information" includes an ID, a password and the like to be used when one of the associates has attempted to access the handwritten content via an external apparatus in order to browse the message of the handwritten content.

Referring back to FIG. 3, when a destination is specified by the destination specifier 205 and transmission of a message is set, the message generator 207 is configured to generate a message about the handwritten content. Note that the message may include the handwritten content itself or the message may be configured to encourage the corresponding associate to access the handwritten content. When a destination is specified by the destination specifier 205 and a phone call transmission (an outgoing phone call) is set, the outgoing call control information generator 208 is configured to generate outgoing call control information (calling control information) for causing a telephone apparatus (may be a built-in telephone function of the message board 2 or an externally provided telephone apparatus) to execute an outgoing phone call process. The message transmitter 209 is configured to transmit the message generated by the message generator 207 to an address of a message destination, and record a history of the transmission in the transmission-reception/calling log 211. The phone call transmitter 210 is configured to transmit an outgoing phone call based on the outgoing call control information generated by the outgoing call control information generator 208, and record a history of the outgoing phone call in the transmission-reception/calling log 211. FIGS. 4A to 4D illustrate respective example of the data structures of the transmission-reception/calling log 211 that includes items such as "date and time", a "transmission/reception type", "counterpart address/phone number", a "message content", "unread/read", and the like. The "date and time" indicate date and time on which a message is transmitted or received, or a message call is transmitted or received. The reception of the message is described later; however, a message may be externally transmitted to the message board 2 (from an external apparatus) to be displayed on the message board 2. The "transmission/reception type" indicates classification of transmission or reception of the message or the phone call. The "counterpart address/phone number" indicates an address of a counterpart of the transmission or reception of the message or the phone number to call. The "message content" is a content of the message received or transmitted (or an audio content of the message in a case of the phone call). The "unread/read" indicates whether an operation to read the received message has performed via the message board 2.

Referring back to FIG. 3, the message board 2 includes an external access processor 212, a message receiver 213, a message display part 214, and a read record manager 215. The external access processor 212 receives access from the PC 8 or the mobile terminal 9 of the associate, authenticates the PC 8 or the mobile terminal 9 by referring to authentication information in the destination database 206, and allowing, upon successful authentication, the PC 8 or the mobile terminal 9 to browse the handwritten contents accumulated in the handwritten content database 202. The handwritten content database 202 are stored in the message board 2 such that only an external apparatus (the PC 8 or mobile terminal 9) that has been authenticated successfully may be allowed to access the handwritten content or the handwritten content database 202. This indicates that multiple professionals are not managed in a unified manner. Accordingly, it may be possible to minimize external leakage of the information to unassociated parties. In addition, costs for database construction, operation, security management and the like are no longer necessary.

The message receiver 213 is configured to receive a message (mainly a response to the message transmitted from the message board 2) from the PC 8 or the mobile terminal 9 of the associate, and registered the received message in the transmission-reception/calling log 211. The message display part 214 is configured to display the message received by the message receiver 213 on the message board 2. When a viewer has performed an operation to read the message displayed by the message display part 214, the read record manager 215 is configured to cause the message display part 214 to stop displaying the message and register read information in the transmission-reception/calling log 211.

On the other hand, the message board 2 includes a tethering manager 216 and a connected apparatus database 217. The tethering manager 216 is configured to provide an apparatus that has been registered as a connectable apparatus (i.e., an apparatus allowed to have connection to the connected apparatus database 217) with a wireless communication environment among devices 6 present inside the care receiver's house 1. FIGS. 4A to 4D illustrate respective examples of data structures of the connected apparatus database 217 that includes items such as a "model number", a "connection history", and the like. The "model number" indicates information for identifying a model of the device 6 that is allowed to have connection to the connected apparatus database 217. The "connection history" is a history of connections by the device 6. Note that data may be collected by the device 6, managed in the message board 2, and may be referred to from outside parties, which may be performed by a part of the functions of the device 6 or may be performed by an additionally provided function. For example, the results of weight measurement, blood-pressure measurement, and body-temperature measurement may be stored and managed in the message board 2 as Personal Health Records (PHRs). Images captured by smartphones, tablets, cameras and the like possessed by the associates may be stored in the message board 2 as PHRs.

Figure 5:
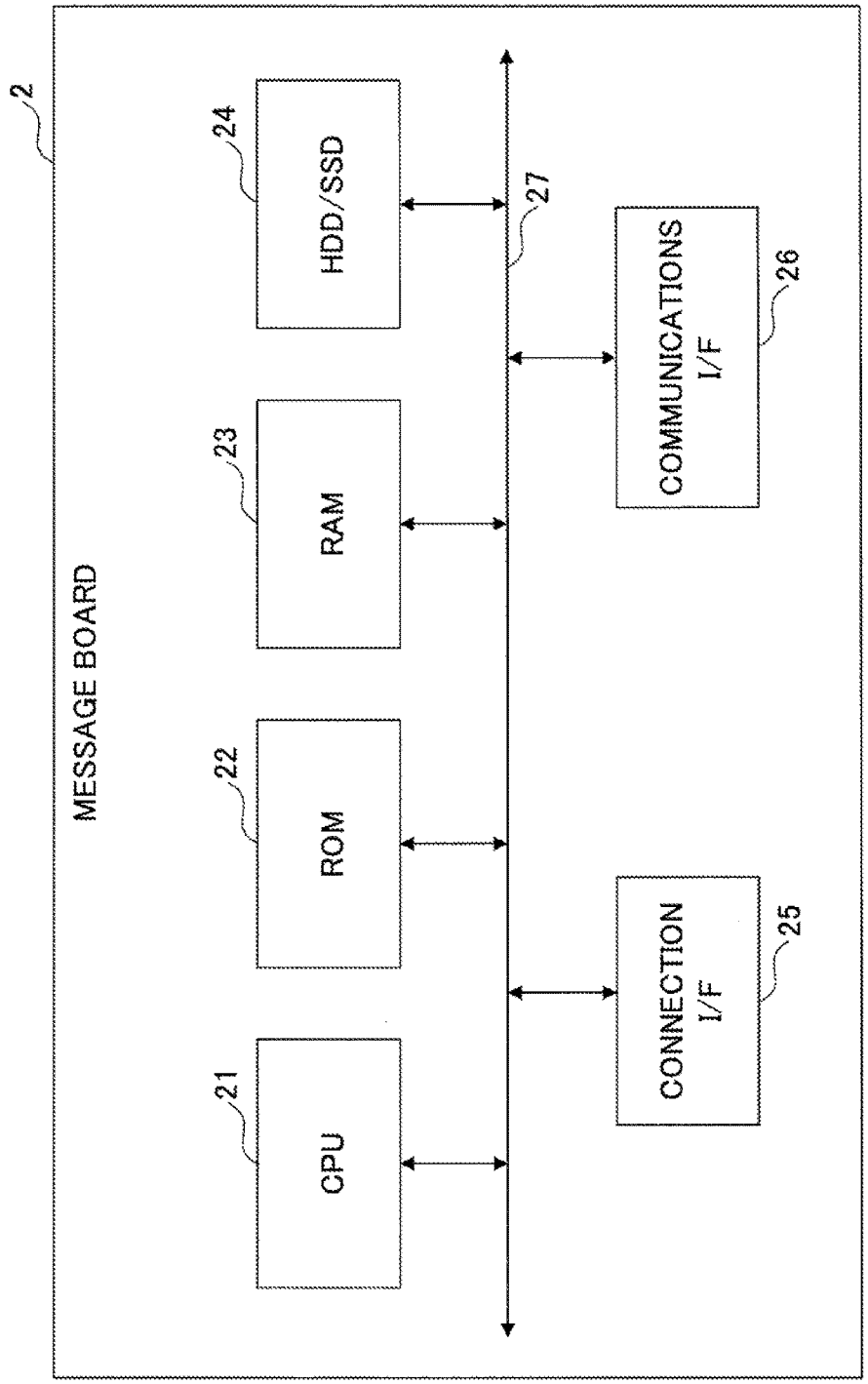
FIG. 5 is a diagram illustrating an example of a hardware configuration associated with information processing in the message board.

FIG. 5 is a diagram illustrating an example of a hardware configuration associated with information processing in the message board 2. The hardware configuration associated with information processing illustrated in FIG. 1 indicates the hardware configuration of the tablet 5. The hardware configuration associated with information processing illustrated in FIG. 2 indicates the hardware configuration of the electronic whiteboard apparatus 20. In FIG. 5, the message board 2 includes a central processing unit (CPU) 21, a read only memory (ROM) 22, a random access memory (RAM) 23, one of a hard disk drive (HDD) 24 and a solid state drive (SSD) 24, a connection interface (I/F) 25, and a communications I/F 26. The CPU 21 is configured to integrally control operations of the message board 2 by executing a program stored in the ROM 22 or in one of the HDD 24 and the SSD 24, using the RAM 23 as a work area. The connection I/F 25 is configured to serve as an interface with an apparatus connected to the message board 2. The communications I/F 26 is an interface for performing communications with other information apparatuses via a network. The function of the message board 2 illustrated in FIG. 3 may be implemented by causing the CPU 21 to execute a predetermined program. Such a program may be acquired via a recording medium or through the network.

Operations

Figure 6:
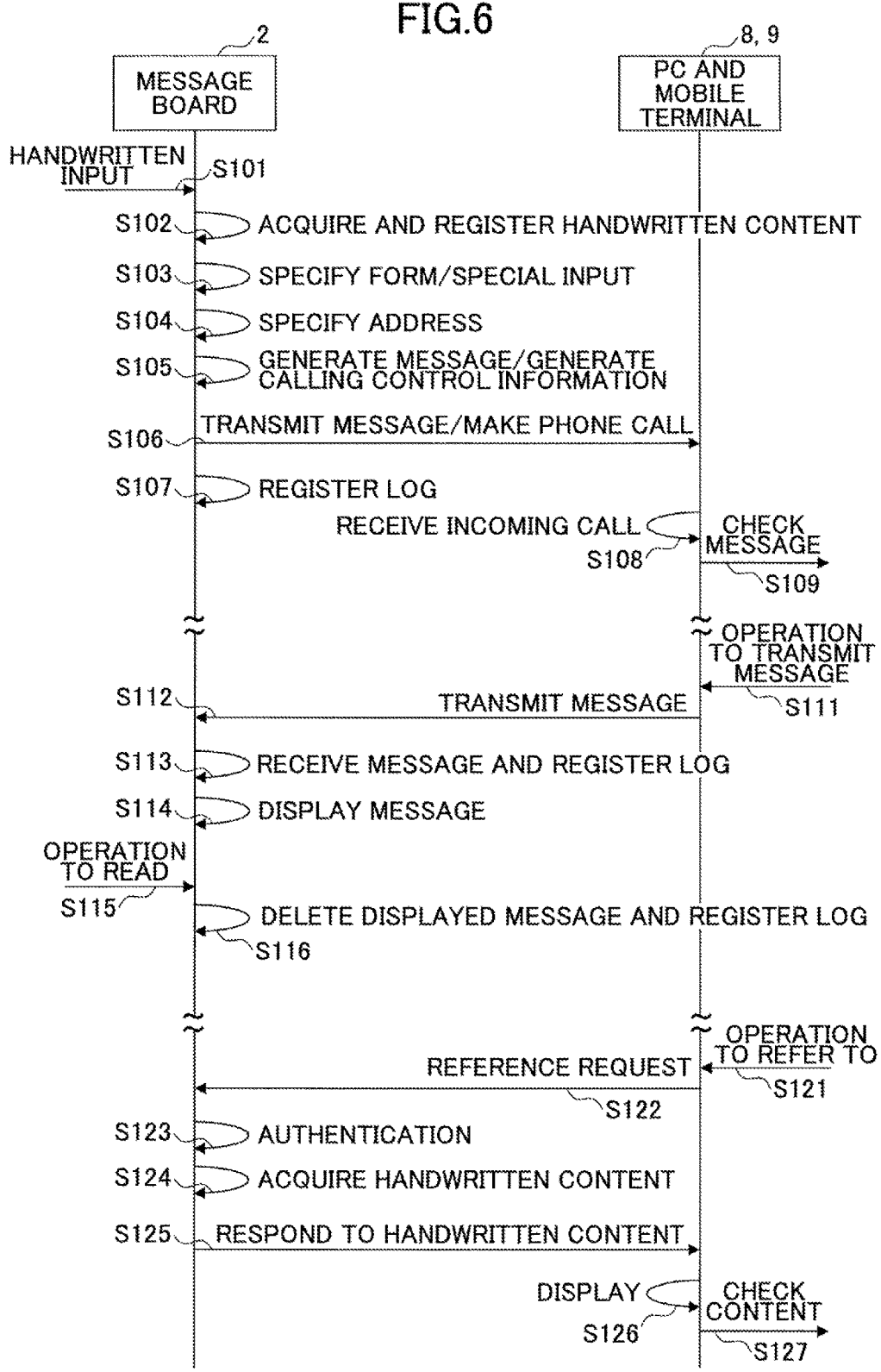
FIG. 6 is a sequence diagram illustrating an example of processing according to an embodiment.

FIG. 6 is a sequence diagram illustrating an example of processing according to the embodiment. In FIG. 6, when the message board 2 receives handwritten input operated by one of the associates inside the care receiver's house 1 (step S101), the handwritten content acquisition part 201 acquires a handwritten content (including handwritten characters, drawings, and the color of the characters) and registers the acquired handwritten content in the handwritten content database 202 (step S102). For example, when the handwritten content acquisition part 201 acquires the handwritten content as image information, the handwritten content acquisition part 201 determines that handwriting has started based on a change detected in the imaged content. When no change is detected for a predetermined time, the handwritten content acquisition part 201 determines that a sequence of the handwriting has completed and acquires an image of a handwritten surface at this moment. When the handwritten content is acquired as trajectory information, the handwritten content acquisition part 201 acquires continuous contact positions of a pen that has completed the handwritten input by detecting no change for the predetermined time since the change has been detected. The handwritten content acquisition part 201 may acquire character information by conducting character recognition on the acquired image information or trajectory information. Note that the handwritten content on the message board 2 may be erased voluntarily (the content registered in the handwritten content database 202 is not deleted in principle). A predetermined area of the message board 2 (e.g., a predetermined a lower left area of the message board 2) may be determined to be a place in which characters are written but from which the written characters are not acquired, and the predetermined area of the message board 2 may be used for communication with the neighbor.

Figure 7:
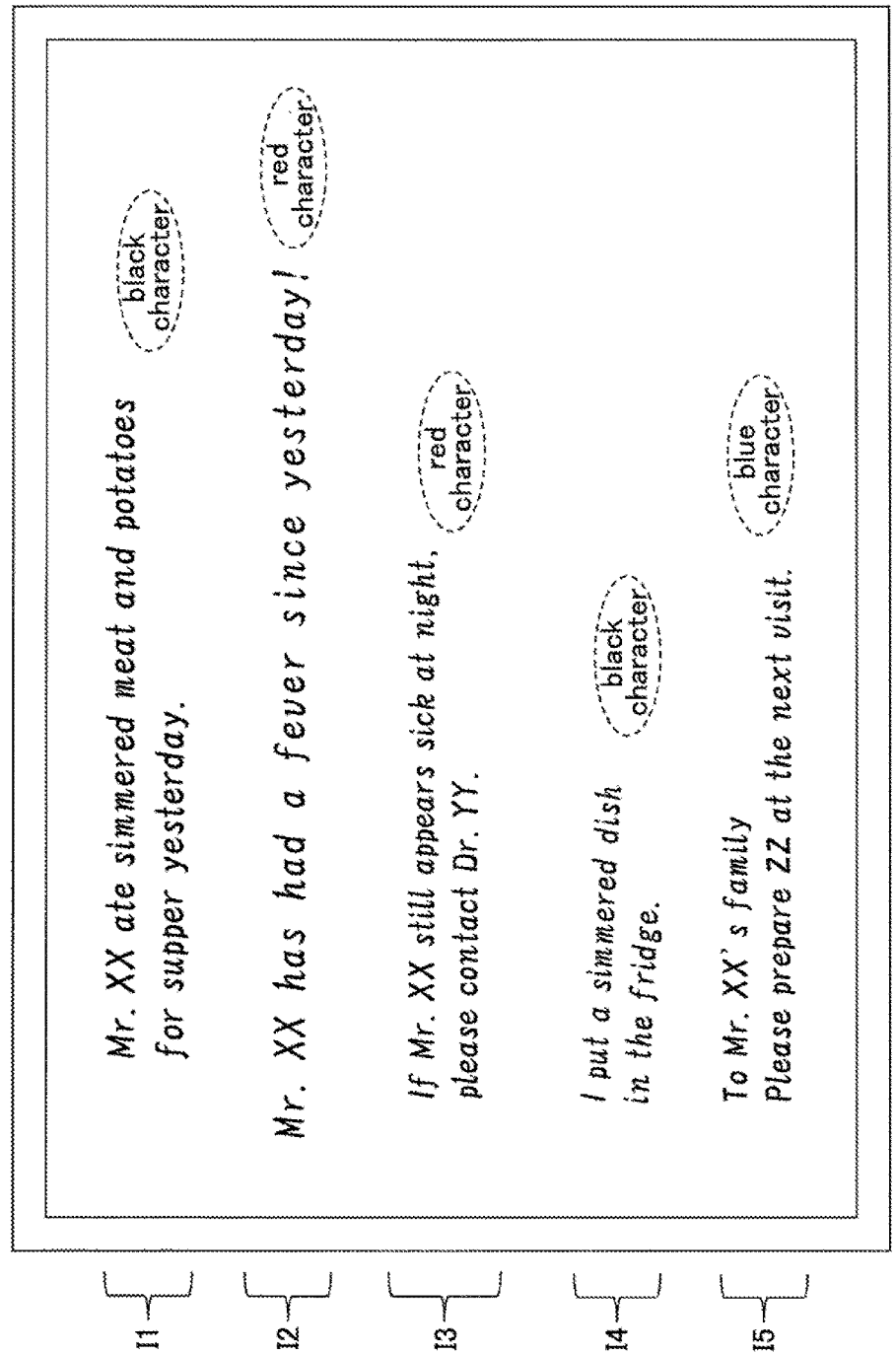
FIG. 7 is a first diagram illustrating an example of handwritten input.
Figure 8:
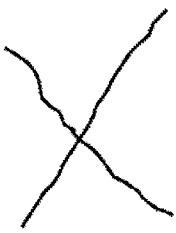
FIG. 8 is a second diagram illustrating an example of handwritten input.

FIG. 7 illustrates examples of the handwritten inputs (i.e., handwritten messages in this case); I1 represents a message in black characters, "Mr. XX ate simmered meat and potatoes for supper yesterday", I2 represents a message in red characters, "Mr. XX has had a fever since yesterday!", I3 represents a message in red characters, "If Mr. XX still appears sick at night, please contact Dr. YY", and I4 represents a message in black characters, "I put a simmered dish in the fridge". Note that the message written with an ink pen is displayed on a display with its original handwriting. The message input with an electronic pen is, however, displayed on a display in a form of the recognized characters; that is, the recognized character strings are converted into respective sets of fonts and displayed at positions at which the characters are written on the message board 2 with the electronic pen. Alternatively, the sets of fonts may be enumerated in a chronological order from the upper left side of the message board 2. FIG. 8 illustrates a handwritten content "x" on the message board 2 indicated by I6. This handwriting method, that is, writing by hand on the message board 2 may be easily handled by anybody without difficulty in operability of a device, regardless of age, inexperience, and the like, compared to the tablet 5.

Subsequently, referring back to FIG. 6, the handwritten form specifier 203 specifies a "form" or a "special input" from a handwritten content newly acquired by the handwritten content acquisition part 201 (step S103). For example, in FIG. 7, the handwritten form specifier 203 specifies the form "black character" with respect to I1, the form "red character" with respect to I2, the form "red character" with respect to I3, the form "black character" with respect to I4, the form "blue character" with respect to I5, and in FIG. 8, the handwritten form specifier 203 specifies the special input "x" with respect to I6.

Subsequently, referring back to FIG. 6, the destination specifier 205 refers to the destination database 206 to acquire an address of a destination in association with the form specified by the handwritten form specifier 203 or the special input specified by the special input determiner 204 (step S104). In the example of FIG. 7, when the form "red character" is specified as a setting of message transmission to the primary doctor and the form "blue character" is specified as a setting of message transmission to the care manager in the destination database 206, respective destinations for transmitting the handwritten contents (messages in this case) indicated by I2, I3, and I5 are specified. The handwritten contents (messages in this case) indicated by I1 and I4 in the form "black character" may be accessible to be referred to from outside but are not transmitted. In the example of FIG. 8, when the special input "x" is specified as a setting of making a phone call to the fire station (ambulance) or the special input "A" is specified as a setting of making a phone call to the family (Mr. XX's family in this case) in the destination database 206, a phone call destination in association with the special input "x" indicated by I6 is specified.

Subsequently, referring back to FIG. 6, when the destination, to which transmission of a message is set, is specified by the destination specifier 205, the message generator 207 generates a message about the handwritten content. When the destination, to which making an outgoing phone call is set, is specified by the destination specifier 205, the outgoing call control information generator 208 generates outgoing call control information to cause a telephone apparatus (including both a built-in telephone function in the message board 2 and an external telephone apparatus) to make an outgoing phone call (step S105). The message transmitter 209 transmits the message generated by the message generator 207, and the phone call transmitter 210 makes an outgoing phone call based on the outgoing call control information generated by the outgoing call control information generator 208 (step S106). In either cases, a history of the message transmission or a history of making an outgoing call is recorded in the transmission-reception/calling log 211 (step S107). In a case of message transmission, when the PC 8 or the mobile terminal 9 of the associate receives an incoming message (step S108), the associate checks the message via the PC 8 or the mobile terminal 9 (step S109). In a case of outgoing phone call making, a telephone apparatus (or telephone function) receives an incoming call, and the associate checks a content of the incoming call via a voice message. Since messages having handwritten contents with high urgency may be transmitted via a mail or transmitted via a telephone call, information may be shared in real time.

Subsequently, when the associate performs a message transmission operation as a response of the associate to the checked message (step S111), the PC 8 or the mobile terminal 9 of the associate transmits a message for the message board 2 (step S112). The message receiver 213 of the message board 2 that has received the message from the PC 8 or the mobile terminal 9 of the associate registers content of the message in the transmission-reception/calling log 211 (step S113). The message display part 214 subsequently displays the message received via the message receiver 213 on the message board 2 (step S114). FIG. 9 depicts the message board 2 displaying the handwriting content "Mr. XX has had a fever since yesterday" on the message board 2 indicated by I2 that has been transmitted to the primary doctor, and the tablet 5 displaying a message "I will come and see Mr. XX around 9:00 AM" transmitted from the primary doctor as a response to the handwriting content I2 on the message board 2.

Subsequently, referring back to FIG. 6, when a viewer of the displayed message performs an operation to read the message (step S115) such as tapping "check" button displayed on the tablet 5 in FIG. 9, the read record manager 215 stops displaying the message on the message display part 214 and registers read information (information about the message being already read) in the transmission-reception/ calling log 211 (step S116).

On the other hand, when the associate performs a reference operation to check the handwritten content on the message board 2 (step S121), the PC 8 or the mobile terminal 9 transmits a reference request to the message board 2 (step S122). To check the handwritten content includes a) to check the details of the handwritten content when the transmitted message does not include the details of the handwritten content, and b) to check a handwritten content that has not been transmitted to the associate. In this case, the associate inputs an ID and a password when performing a reference operation. The external access processor 212 of the message board 2 that has received access from the PC 8 or the mobile terminal 9 of the associate performs authentication by referring to authentication information in the destination database 206 (step S123). When the PC 8 or the mobile terminal 9 of the associate is successfully authenticated, the handwritten content is acquired from the handwritten content database 202 (step S124), and transmitted to the PC 8 or the mobile terminal 9 as a response (step S125). In this step, the acquired handwritten content may be transmitted immediately. Alternatively, a list of the accumulated handwritten contents may be transmitted, and only the details of those handwritten contents requested may be transmitted. Further, based on the reference history of the associate, the handwritten contents to be transmitted may be limited only to the unread handwritten contents. The PC 8 or the mobile terminal 9 that has received handwritten content as the response displays the content (step S126), and the associate checks the displayed content (step S127). The above-described technology may allow the primary doctors, the visiting nurses, care managers, and the like to access from anywhere and refer to information that could not have been obtained unless they were in the place in a case of a paper-based communication notebook, thereby leading to reduction in burdens on the primary doctors, the visiting nurses, care managers, and the like.

Outline

According to the disclosed embodiments, there is provided a technology capable of simply transmitting a message for a desired destination.

The preferred embodiments are described above. The embodiments of the present invention are illustrated with specific examples; however, the present invention is not limited to these examples, and various alterations or changes may be made without departing from the gist and the scope of the claims of the present invention. Specifically, the present invention shall not be construed as being limited to details of the specific examples and accompanying drawings thereof.

According to the disclosed embodiments, it is possible to simply transmit a message for a desired destination.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority or inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable recording medium having stored therein a message information generating program, which when processed by one or more processors, causes a computer to execute a process comprising:

acquiring first information having both a character string input by handwriting and a character color related to the character string input by the handwriting as a handwritten input content on an electronic message board;

specifying a form of the character string based on the color related to the character string acquired first information;

specifying an address associated with the specified form by referring to a storage configured to store an address of a message destination in association with a form of a character string; and generating and sending message information with the specified address as a destination, the message information including second information corresponding to the character string.

2. The non-transitory computer-readable storage medium according to claim 1, the process further comprising:

holding the first information in an apparatus to which the first information is input; and allowing, upon successful authentication, an external apparatus to access the first information when the external apparatus has attempted to access the first information.

3. The non-transitory computer-readable storage medium according to claim 1, the process further comprising:

acquiring the first information in one of forms including image information, trajectory information, and character information.

4. The non-transitory computer-readable storage medium according to claim 1, the process further comprising:

displaying a response or a new message that has been received from an external apparatus associated with the address of the message destination.

5. A non-transitory computer-readable storage medium having stored therein an outgoing call control program, which when processed by one or more processors, causes a computer to execute a process comprising:

acquiring information including one of a character, a symbol, and a mark input by handwriting on an electronic message board;

specifying a type of the information based on the acquired information;

specifying a phone number associated with the specified type of the information by referring to a storage configured to store a phone number of an outgoing call destination in association with a type of the information; and generating outgoing call control information for causing a telephone apparatus to execute an outgoing call process to the specified phone number.

6. The non-transitory computer-readable storage medium according to claim 5, the process further comprising:

holding the information in an apparatus to which the information is input; and allowing, upon successful authentication, an external apparatus to access the information when the external apparatus has attempted to access the information.

7. The non-transitory computer-readable storage medium according to claim 5, the process further comprising:

acquiring the information in one of forms including image information, trajectory information, and character information.

8. The non-transitory computer-readable storage medium according to claim 5, the process further comprising:

displaying a response or a new message that has been received from an external apparatus associated with the phone number of outgoing call destination.

9. A message information generating apparatus comprising:

one or more processors programed to execute a process including acquiring first information having both a character string input by handwriting and a character color related to the character string input by the handwriting on an electronic message board;
specifying a form of the character string based on the color related to the character string acquired first information;
specifying an address associated with the specified form by referring to a storage configured to store an address of a message destination in association with a form of a character string; and
generating and sending message information with the specified address as a destination, the message information including second information corresponding to the character string.

10. The message information generating apparatus according to claim 9, the process further comprising:
holding the first information in an apparatus to which the first information is input; and
allowing, upon successful authentication, an external apparatus to access the first information when the external apparatus has attempted to access the first information.

11. The message information generating apparatus according to claim 9, the process further comprising:
acquiring the first information in one of forms including image information, trajectory information, and character information.

12. The message information generating apparatus according to claim 9, the process further comprising:
displaying a response or a new message that has been received from an external apparatus associated with the address of the message destination.

13. A message information generating method executed by a computer, the message information generating method comprising:
acquiring first information having both a character string input by handwriting and a character color related to the character string input by the handwriting on an electronic message board;
specifying a form of the character string based on the color related to the character string acquired first information;
specifying an address associated with the specified form by referring to a storage configured to store an address of a message destination in association with a form of a character string; and
generating and sending message information with the specified address as a destination, the message information including second information corresponding to the character string.

14. The message information generating method according to claim 13, further comprising:
holding the first information in an apparatus to which the first information is input; and
allowing, upon successful authentication, an external apparatus to access the first information when the external apparatus has attempted to access the first information.

15. The message information generating method according to claim 13, further comprising:
acquiring the first information in one of forms including image information, trajectory information, and character information.

16. The message information generating method according to claim 13, further comprising:
displaying a response or a new message that has been received from an external apparatus associated with the address of the message destination.

\* \* \* \* \*